United States Patent [19]

Hansson et al.

[11] Patent Number: 5,208,019

[45] Date of Patent: May 4, 1993

[54] USE OF GAMMA-INTERFERON FOR THE TREATMENT OF VASCULAR STENOSIS

[76] Inventors: Göran Hansson, Dr Linds gata 6, S-413 25 Göteborg; Jan Holm, Änggardsplatsen 8, S-413 19 Göteborg; Lena Jonasson, Gröna gatan 8, S0575 33Eksjö, all of Sweden

[21] Appl. No.: 671,786

[22] PCT Filed: Sep. 27, 1989

[86] PCT No.: PCT/SE89/00520
  § 371 Date: May 17, 1991
  § 102(e) Date: May 17, 1991

[87] PCT Pub. No.: WO90/03189
  PCT Pub. Date: May 5, 1990

[30] Foreign Application Priority Data

Sep. 30, 1988 [SE] Sweden ................ 8803472-3

[51] Int. Cl.$^5$ .................. A61K 37/66; C07K 15/26
[52] U.S. Cl. .................. 424/85.5; 424/85.4; 530/351
[58] Field of Search .............. 424/85.5, 85.4

[56] References Cited

U.S. PATENT DOCUMENTS

| | | | |
|---|---|---|---|
| 4,483,849 | 11/1984 | Carter et al. | 424/85.5 |
| 4,680,175 | 7/1987 | Estis et al. | 424/85.4 |
| 4,897,264 | 1/1990 | Novick et al. | 424/85.5 |
| 4,946,674 | 8/1990 | von Eichborn et al. | 424/85.5 |
| 5,026,544 | 1/1991 | Albrecht et al. | 424/85.5 |
| 5,096,705 | 3/1992 | Goeddel et al. | 424/85.5 |

OTHER PUBLICATIONS

Arakawa et al. (1985) J. Biol. Chem. 260(27):14435–14439.
Jonasson et al. (Mar., 1988) Lab. Invest. 58(3):310–315.

*Primary Examiner*—Robert A. Wax
*Assistant Examiner*—Richard C. Ekstrom
*Attorney, Agent, or Firm*—Kane Dalsimer Sullivan Kurucz Levy Eisele & Richard

[57] ABSTRACT

The present invention relates to the use of gamma-interferon for the preparation of a pharmaceutical preparation for the treatment of vascular stenosis caused by e.g. intimal hyperplasia, including the treatment of restenosis following treatment of arterial stenosis or occlusion.

In a preferred embodiment the present invention relates to the use of gamma-interferon for the treatment of arterial stenosis following vascular surgery and/or angioplasty.

5 Claims, 4 Drawing Sheets

USE OF GAMMA-INTERFERON FOR THE TREATMENT OF VASCULAR STENOSIS

The present invention is directed to the use of gamma-interferon for the preparation of a pharmaceutical preparation for the treatment of vascular stenosis caused by e.g. intimal hyperplasia, including the treatment of restenosis following angioplasty and/or vascular surgery. The present invention is especially directed to the treatment of arterial stenosis following angioplasty and/or vascular surgery.

BACKGROUND OF THE INVENTION

Progress in cardiovascular research has made it possible to reduce the incidence of heart attacks in patients principally by reducing the risk factors for atherosclerosis, such as hypercholesterolemia, smoking, and hypertension. It is known that the development of a heart attack can be stopped by administering tissue-type plasminogen activator (t-PA), which dissolves the thrombus in the coronary artery. Recently, the cloning and production of t-PA by recombinant DNA techniques has made it possible to produce t-PA in unlimited quantities.

For prevention of heart attacks in patients who have developed coronary atherosclerosis, there are, however, only surgical methods available. Several important new techniques have been developed for surgical therapy. In particular, angioplastic procedures using balloon catheters, and more recently lasers, have made it possible to treat patients with less severe symptoms, where coronary bypass surgery is not warranted, and also patients whose general condition is too poor to permit major surgery.

All manipulations of major blood-vessels, be it conventional surgery or angioplastic procedures, are, however, hampered by the frequent occurrence of intimal hyperplasia leading to restenosis of the artery. For example, approximately 30% of all patients who undergo percutaneous transluminal coronary angioplasty at Sahlgren's Hospital, Gothenburg, Sweden, develop intimal lesions that give rise to ischemic symptoms.

The problem is also observed after conventional vascular surgery. Reconstructive surgery of the arteries, that supply the lower extremities with blood is followed by a recurrence of the ischemic symptoms, due to intimal lesions, in 50% of all cases. (See Rutherford R. (ed). Vascular Surgery. Ch. 58. 2nd ed., Saunders, 1984.) Similarly, approximately 20% of all patients who undergo carotid endarterectomy develop intimal hyperplasia. Similar results have been reported from several other treatment centers. Intimal hyperplasia is also often observed in connection with coronary bypass surgery. Postoperative and "postangioplastic" intimal hyperplasia is therefore today a major problem in clinical cardiology, heart surgery and vascular surgery.

For example, many patients with angina pectoris will have to undergo repeated angioplastic procedures, and coronary bypass surgery may eventually have to be performed. It is clear that if one could stop the development of intimal hyperplasia, it would be possible to save patients from muc pain and suffering and also to reduce the costs of treatment substantially.

The mechanisms underlying intimal cell proliferation have been meticulously studied by vascular biologists. It is known that mechanical injury to the artery results in migration-of medial smooth muscle cells into the intima. Once in the intima, the cells begin to proliferate, forming an intimal lesion that persists for months. (See Schwartz S. M., Campbell GR, Campbell J. H. Circ Res 58:427, 1986.) Reendothelialization of the surface seems to be important for regression of the lesion, and both the endothelial area involved and the amount of damage to subendothelial structures are important for the progression of the lesion.

The proliferation of vascular smooth muscle cells is probably controlled by growth factors that either circulate in the blood, such as insulin, or are released from cells, such as the platelet-derived growth factor. The latter factor is synthesized not only by megakaryocytes but also by monocytes and endothelial cells (see Ross R. New Engl J Med 314:488, 1986 and Ross R., Raines E. W., Bowen-Pope D. F. Cell 1986:46:155–169), and this implies that inflammatory cells might participate in the growth regulation of the vessel wall.

Much less is known about growth-inhibiting factors for smooth muscle cells. Heparin administered pharmacologically inhibits smooth muscle profileration (see Clowes A. W, Karnovsky M. J. Nature 265:625, 1977), and it has been suggested that endogenous heparin-like substances may be involved in physiologic growth control. It should, however, be noted that all patients who undergo angioplastic and surgical treatment are under heparin therapy, and yet develop significant intimal stenosis.

Recent immunocytochemical studies using cell types-pecific monoclonal antibodies have shown that monocyte-derived macrophages are present in large numbers in the atherosclerotic plaque. (See Vedeler C. A., Nyland H., Matre R.: In situ characterization of the foam cells in early human atherosclerotic lesions. Acta Pathol Microbiol Immunol Scand (C) 1984:92:133–137, Aqel N. M., Ball R. Y., Waldman H, Mitchinson M. J.: Monocytic origin of foam cells in human atherosclerotic plaques. Atherosclerosis 1984:53:265–271, Jonasson L., Holm J., Skalli O., Bondjers G., Hansson G. K.: Regional accumulations of T cells, macrophages and smooth muscle cells in the human atherosclerotic plaque. Atherosclerosis 1986:6:131–140 and Gown A. M., Tsukada T., Ross R.: Human atherosclerosis. II. Immunocytochemical analysis of the cellular composition of human atherosclerotic lesions. Am J Pathol 1986:125:191–207.) They are, however, not the only blood-borne cells that can be found in the arterial wall under pathological circumstances. T lymphocytes constitute one fifth of the cell population in the fibrous cap of the human atherosclerotic plaque (see Jonasson et al, Atherosclerosis 1986:6:131–140), and they can also be observed in experimental models of vascular injury. (See Jonasson L., Holm J., Hansson G. K.: Smooth muscle cells express Ia antigens during arterial response to injury. Lab Invest 1988:58:310–315.)

Immunocytochemical data suggest that T lymphocytes can modulate the growth properties and other functions of smooth muscle cells. In atherosclerotic plaques, where T lymphocytes are abundant, many smooth muscle cells express class II major histocompatibility complex antigens (Ia antigens). On the other hand smooth muscle cells lack Ia antigens in nonatherosclerotic, normal arteries. (See Jonasson L., Holm J., Skalli O., Gabbiani G., Hansson G. K.: Expression of class II transplantation antigen on vascular smooth muscle cells in human atherosclerosis. J Clin Invest 1985:76:125–131 and Hansson G. K., Jonasson L., Holm J., Claesson-Welsh L. Class II MHC antigen expression in the atherosclerotic plaque; smooth muscle cells express HLA-DR, HLA-DQ, and the invariant gamma chain. Clin exp Immunol 1986:64:261-268.) It has been shown that Ia antigens appear on smooth muscle cells during the arterial response to injury in rats, but there is no prior work showing or suggesting a relation between Ia antigens and vascular stenosis.

These antigens play a basic role in the presentation of foreign antigens to T lymphocytes. Their expression by macrophages, endothelial cells, and several other cell types is induced by gamma-interferon secreted by activated T lymphocytes. (See Pober J. S, Gimbrone M. A., Cotran R. S., Reiss C. S., Burakoff S. J., Fiers W., Ault K.A.: Ia expression by vascular endothelium is inducible by activated T cells and by human gamma-interferon. J Exp Med 1983:157: 1339-1353 and Unanue E. R., Allen P. M.: Comment on the finding of Ia expression in non-lymphoid cells. Lab Invest 1986: 55:123-125.)

Alfa- and beta-type interferons, which are produced by leukocytes, fibroblasts, and other cell types, are known to inhibit the proliferation of certain cell types. Gamma-interferon is released by activated T lymphocytes, and it also has been shown to inhibit proliferation when conditioned media or purified preparations are added to culture cells of various types, such as mammary gland cells and fibroblasts. (See Rubin B. Y., Gupta S. L.: Differential efficacies of human type I and type II interferons as antiviral and antiproliferative agents. Proc Natl Acad Sci USA 1980: 77:5928-5932, Blalock J. E., Georgiades J. A., Langford N. F., Johnson H. M.: Purified human immune interferon has more potent anticellular activity than fibroblast or leukocyte interferon. Cell Immunol 1980:49:390-394 and Wahl S. M., Galtely C. L.: Modulation of fibroblast growth by a lymphokine of human T cell and continuous T cell line origin. J Immunol 1983:130: 1226-1230.) However, it has been questioned whether this effect might be due to contaminations of the preparations with lymphotoxin (tumornecrosis factor) rather than an inhibitory effect of gamma-interferon itself.

Summing up it would be advantageous to be able to treat vascular stenosis and related disorders by use of preparations that inhibit growth of smooth muscle cells.

BRIEF DESCRIPTION OF THE INVENTION

It has now surprisingly been found, and this forms the basis for the present invention, that gamma-interferon is an important growth inhibitor for smooth muscle cells in intimal lesions as well as in atherosclerosis.

One aspect of the present invention provides the use of gamma-interferon for the preparation of a pharmaceutical preparation for the treatment of vascular stenosis caused by e.g. intimal hyperplasia.

In one embodiment of this aspect of the invention the treatment of vascular stenosis is the treatment of restenosis following the treatment of arterial stenosis or occlusion.

In a preferred embodiment of this aspect of the invention the treatment of vascular stenosis is the treatment of arterial stenosis following angioplasty and/or vascular surgery.

Another aspect of the present invention provides a method of using gamma-interferon for the treatment of vascular stenosis caused by e.g. intimal hyperplasia, wherein gamma-interferon is administered to a patient in a pharmaceutical preparation containing said interferon in a sufficient amount to produce a therapeutical effect.

In one embodiment of said aspect of the invention the treatment of vascular stenosis is the treatment of restenosis following the treatment of arterial stenosis or occlusion.

In a preferred embodiment of said aspect of the invention the treatment of vascular stenosis is the treatment of arterial stenosis following angioplasty and/or vascular surgery.

The source of gamma-interferon used is not critical and may be synthetic, native or recombinant gamma-interferon, produced by recombinant DNA techniques.

The present pharmaceutical preparation is preferably given to patients by parenteral administration; i.e. by subcutaneous, intravenous or intramuscular injection.

The diluents and excipients are those conventionally used in pharmacy, for example a physiological saline solution.

DETAILED DESCRIPTION OF THE INVENTION

Figure 1:
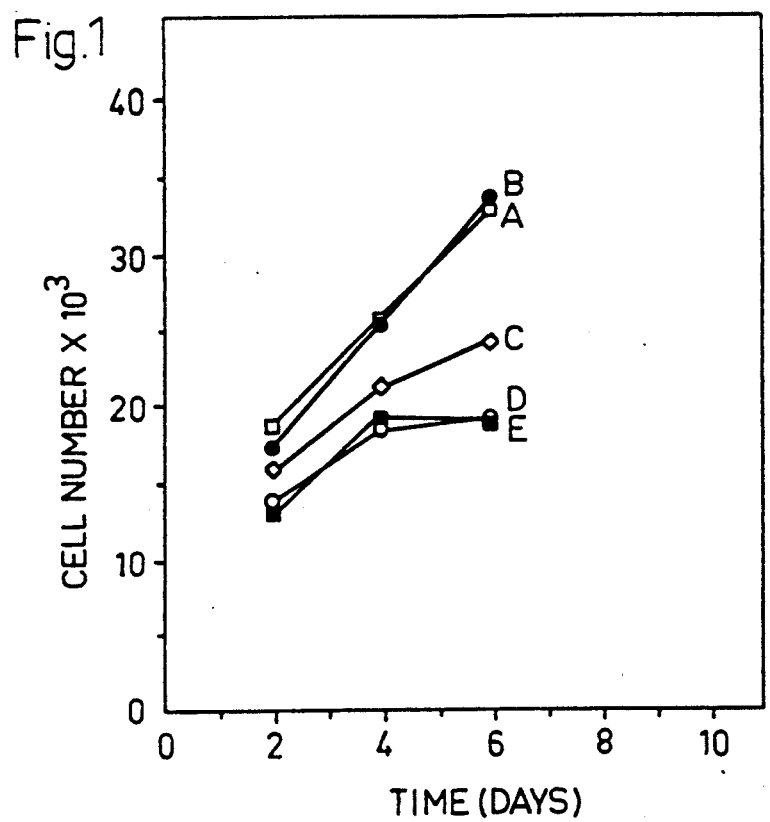
FIG. 1 is a graph showing the effect of various concentrations of gamma-interferon on smooth muscle culture cell proliferation.

The effect of recombinant gamma-interferon on cultured arterial smooth muscle cells has been studied and it was found that this lymphokine inhibits cellular proliferation. This effect is parallelled by an induction of Ia antigens. Therefore, Ia expression and cell replication was studied in the arterial response to injury in the ballooned rat carotid artery. Evidence for a correlation between Ia expression and lack of proliferation was obtained.

Efforts were made to identify the cell populations that form the atherosclerotic plaque. Monoclonal antibodies to cell type-specific antigens were therefore applied to sections of endarterectomy specimens. Most cells in the lipid rich core region were found to stain with antibodies to macrophage antigens, and many of the cells of the fibrous cap were often stained by anti-smooth muscle antibodies. (See Jonasson L., Holm J, Skalli O., Bondjers G., Hansson G. K. Arteriosclerosis 6:131, 1986.) In addition and more surprisingly, substantial amounts of T lymphocytes, particularly in the fibrous cap was observed. Many of them showed signs of activation, i.e., expression of HLA-DR, VLA-1, and the interleukin-2 receptor. (See e.g. Jonasson L., Holm J., Skalli O., Gabbiani G., Hansson G. K. J Clin Invest 76:125, 1985 and Hansson G. K., Jonasson L., Holm J., Claesson-Welsh L. Clin exp Immunol 64:261, 1986.)

Many smooth muscle cells in these T cell-rich areas expressed HLA-DR (Ia antigens), whereas such antigens were never found on smooth muscle cells of the normal arterial wall. HLA-DR expression is induced by activated T cells via release of gamma-interferon (see Pober J. S. S. et al. Nature 305:726, 1983 and Unanue E. R., Allen P. M. Lab Invest 55:123, 1983). The findings in atherosclerosis therefore suggest that gamma-interferon is involved in a paracrine regulation of gene expression in the atherosclerotic plaque. Furthermore direct immunohistochemical evidence for the presence of gamma-interferon in the atherosclerotic plaque has recently been obtained.

Experimental procedure

An experimental animal model was used for analysis of the role of T lymphocytes in regulating arterial smooth muscle proliferation and gene expression. The balloon catheter model developed by Baumgartner and improved by Clowes and Reidy was adopted for this purpose. Intimal lesions were induced in the rat carotid artery by a Fogarty balloon catheter, and the infiltration of different types of leukocytes and expression of Ia antigens was analyzed by immunohistochemistry at different time points after injury.

A small but significant amount of T cell infiltration was found in two weeks, and it was also found that smooth muscle cells in the intima started to express Ia antigens. In vitro, Ia expression could be induced by recombinant gamma-interferon. These findings suggest that gamma-interferon is released, and affects smooth muscle gene expression, in the intimal lesions.

In vitro, gamma-interferon is an efficient inhibitor of smooth muscle cell proliferation, and it is thus believed that it may serve as an endogenous inhibitor of smooth muscle proliferation in the intimal lesion after injury. Indirect support for this hypothesis was obtained by analysis of smooth muscle cell replication in the lesion. It was found that Ia-positive smooth muscle cells did not take up $^3$H-thymidine during a 24-hour pulse at 14 days post injury.

In another set of experiments, all replicating smooth muscle cells were labeled with $^3$H-thymidine via an osmotic pump introduced at the time of ballooning. By combined $^3$H autoradiography and immunohistochemical staining for Ia, it was found that cells which expressed Ia at the time of sacrifice, i.e., at day 14 post ballooning, had undergone significantly fewer cycles of replications than Ia-negative smooth muscle cells. This supported the belief that gamma-interferon is an endogenous inhibitor of smooth muscle cell replication in intimal hyperplasia. Encouraged by these results, it was decided to continue the work by testing the effect of parenterally administered gamma-interferon on the arterial response to injury.

Materials and methods

Cell culture

Rat aortic smooth muscle cells (SMCs) were isolated from 200-g male Sprague-Dawley rats by collagenase digestion and grown in RPMI-1640 medium supplemented by fetal calf serum (FCS), 100 units/ml penicillin G, 100 μg/ml streptomycin, and 50 μg/ml ascorbic acid. Third to fifth passage cells were used for the experiments, and they were plated in 96-well microtiter plates (Nunc, Roskilde, Denmark) for growth analysis, or in 10-cm$^2$ Petri dishes for analysis of DNA synthesis.

Growth analysis

SMCs were either growing exponentially or were induced to enter the gap 1 ($G_1$) phase of the cell cycle by addition of 10% FCS after 48 hours of serum starvation in 0.5% FCS. Cultures were exposed to recombinant mouse gamma-interferon (Genentech. South San Francisco, Calif.) added to the medium together with 10% FCS. At various times, they were fixed with 4% formaldehyde in a 0.1M acetate buffer, pH 3.1, and incubated with Amido Black B to stain the cell proteins. Unbound dye was rinsed off by distilled water, and dye uptake was determined at 620 nm in an EIA microtiter photometer. Dye binding per cell was calculated by dividing dye absorbance per culture ($A_{620}$ units) with the cell number per culture, which in turn was determined by hemocytometric counting of trypsinized cells in parallel cultures. Since there was very little variability of dye absorbance per cell in these cultures (<2%), cell numbers could be estimated by dividing the $A_{620}$ absorbance of a given culture with the $A_{620}$/cell coefficient. There was no significant difference in $A_{620}$/cell between gamma-interferon treated and untreated cultures. The correlation between microscopic counting and dye binding analysis for determination of cell numbers was excellent (r=0.98).

DNA Synthesis

DNA synthesis was determined essentially as described by Raines and Ross. In brief, SMC were synchronized in the gap 0 phase ($G_0$) as described above, and then induced to enter the cell cycle by addition of 10% FCS in the presence or absence of gamma-interferon, added simultaneously or at various times after the addition of serum. $^3$H-thymidine (10 μCi/10 cm$^2$ well) was added together with FCS, and the cells were harvested by trypsinization at 24 hours. They were collected on 0.22-μm Millipore filters (Bedford, Mass. ), and trichloroacetic acid-insoluble radioactivity was analyzed in a scintillation counter after solubilization in Insta-gel 1 ®.

Enzyme-Linked Immunoassay of Ia Expression

SMC in 96-well microtiter plates (Nunc) were exposed to gamma-interferon as will be described below. The cells were then rinsed three times with PBS (phosphate-buffered saline, 150 mM NaCl, 15 mM phosphate buffer, pH 7.2), and fixed for 15 minutes at 4° C. with 1% formaldehyde in 100 mM sodium phosphate buffer, pH 7.2. They were rinsed three times with PBS, reacted with 100 mM glycine in PBS with 0.1% bovine serum albumin (BSA; RIA grade, Sigma Chemical, St. Louis, Mo.) for 30 minutes at 37° C. After the cells had been rinsed twice in PBS, they were preincubated for 60 minutes at 37° C. with 0.5% normal horse serum in PBS containing 0.1% BSA, rinsed three times with PBS with 0.05% Tween-20, and incubated with the monoclonal antibodies OX6 and OX17 (Seralab, Crawle Down, Sussex, UK), which detect I-A and I-E antigens, respectively, for 60 minutes at 37° C., at optimal dilutions determined by checkerboard titration. Excess antibody was washed off by rinsing three times with PBS/Tween, and the cells were incubated for 30 minutes with alkaline-phosphatase-labeled, affinity purified goat anti-mouse immunoglobulin G antibodies (Jackson Lab, Avondale, Pa.) diluted 1:1000 in PBS/BSA. After PBS/Tween washes, the specimens were incubated for 60 minutes at 37° C. in a substrate solution containing 1 mg/ml p-nitrophenyl phosphate substrate in 10% diethanolamine, 0.5 mM $MgCl_2$, pH 9.8. The reaction was stopped by addition of 2M NaOH, and the absorbance at 405 nm was determined in the microtiter photometer.

Animal Experiments I

Fifteen 5-month-old Sprague-Dawley rats were subjected to carotid injury as described previously. In brief, anesthetized rats were catheterized with a Fogarty 2F balloon catheter via the left external carotid artery. The balloon was inflated in the proximal part of the common carotid, and the catheter was retracted toward the carotid bifurcation. The procedure was repeated three times, and the catheter was then removed and the external carotid and superficial wound closed. This procedure has been shown to remove all endothelial cells of the wounded area and to produce some loss of medial smooth muscle cells.. $^3$H-thymidine (6.7 Ci/mmol; New England Nuclear, Boston, Mass.) was continuosly infused into five rats from the day of surgery via an intraperitoneal osmotic minipump (see Clowes A. W., Schwartz S. M.: Significance of quiescent smooth muscle migration in the injured rat carotid artery. Circ Res 1985:56:139-145). The other 10 rats were injected with $^3$H-thymidine three times during 24 hours at day 14 (see Jonasson L., Holm J., Hansson G. K.: Smooth muscle cells express Ia antigens during arterial response to injury, Lab Invest 1988:58:310-315).

Fourteen days after surgery, the rats were anesthetized and the carotid arteries fixed by perfusion with 1% formaldehyde in phosphate buffer, pH 7.2. Segments containing the injured left and uninjured right carotid artery were snap-frozen in liquid nitrogen, and 8-μm sections were cut on a cryostat microtome. The Ia antigen I-A was visualized by incubation with the mouse anti-rat monoclonal antibody OX6 followed by biotinylated horse anti-mouse immunoglobulin G and a biotin-avidin-alkaline phosphatase complex (Vector, Burlingame, Calif.). The sections were then fixed in formaldehyde, and dipped in NTB2 nuclear track emulsion (Kodak, Rochester, N.Y.). They were developed after two weeks, stained with hematoxylin, and examined in the light microscope. For each animal, 200 cells were counted in corresponding areas of the intimal thickening, and the proportions of Ia-positive and $^3$H-thymidine-positive cells determined.

Means were compared with Student's t test; in the case of multiple comparisons, Scheffe's correction was used as described by Armitage (see Armitage P.: Statistical Methods in Medical Research. Oxford, England, Blackwell, 1971). Differences were considered significant at $p<0.05$. Regression lines were fitted by least-squares method.

Results

The proliferation of exponentially growing rat smooth muscle cells was inhibited by the presence of recombinant gamma-interferon in the culture medium. With reference to FIG. 1 it is shown that smooth muscle cell proliferation is inhibited by gamma-interferon. Exponentially growing arterial smooth muscle cells in 96-well microtiter plates were exposed to different doses of recombinant murine gamma-interferon (gamma-IFN) in the culture medium. A, B, C, D and E correspond to the concentrations of gamma-interferon in units(u)/ml of 0, 1, 10, 50 and 100, respectively. Significant inhibition was obtained with 10 units/ml after 4 days of treatment and with 50 or 100 units/ml 2 days after interferon addition. There was a dose-response relation between gamma-interferon dose and inhibition of proliferation up to 50 units/ml, when a plateau was reached.

Figure 2:
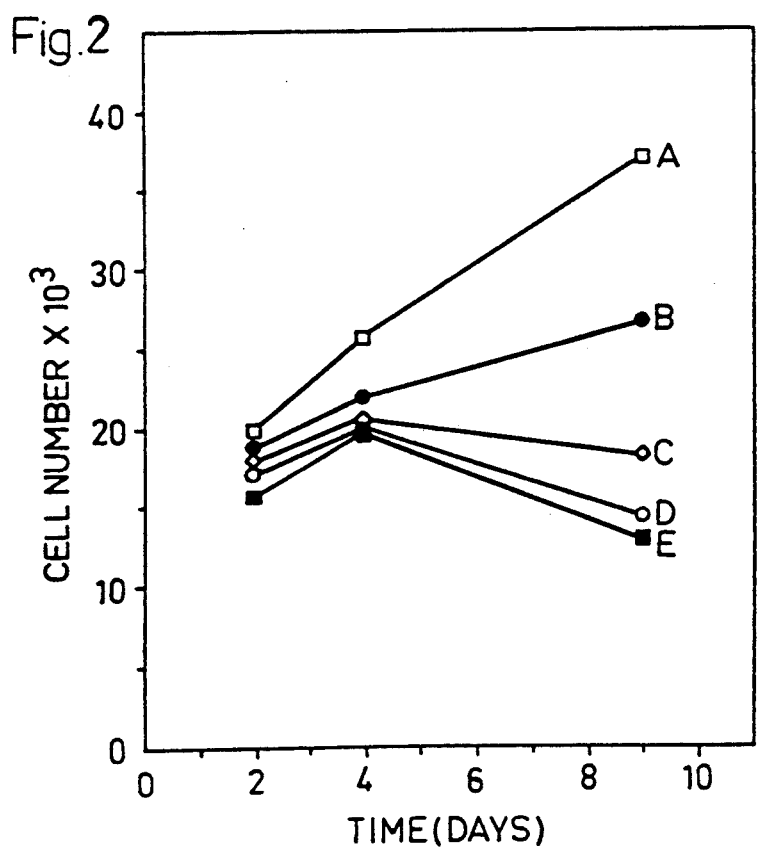
FIG. 2 is a graph showing the effect of various concentrations of gamma-interferon on induction of growth in smooth muscle cell cultures.

The inhibition of growth was even more pronounced when the cells were first growth-inhibited by serum starvation, and then permitted to enter the cell cycle by addition of FCS. This is demonstrated by FIG. 2 showing that induction of growth is synchronized smooth muscle cultures is inhibited by gamma-interferon. A, B, C, D and E correspond to the same gamma-interferon concentrations as A-E in FIG. 1. In this case 10 units/ml gamma-interferon in the medium resulted in a 50% growth inhibition, and a significant inhibition was obtained with as little as 1 unit/ml after 9 days of exposure. A significant inhibition was obtained after 4 days with 10 units/ml, and maximal inhibition was reached with 50 units/ml.

Figure 3:
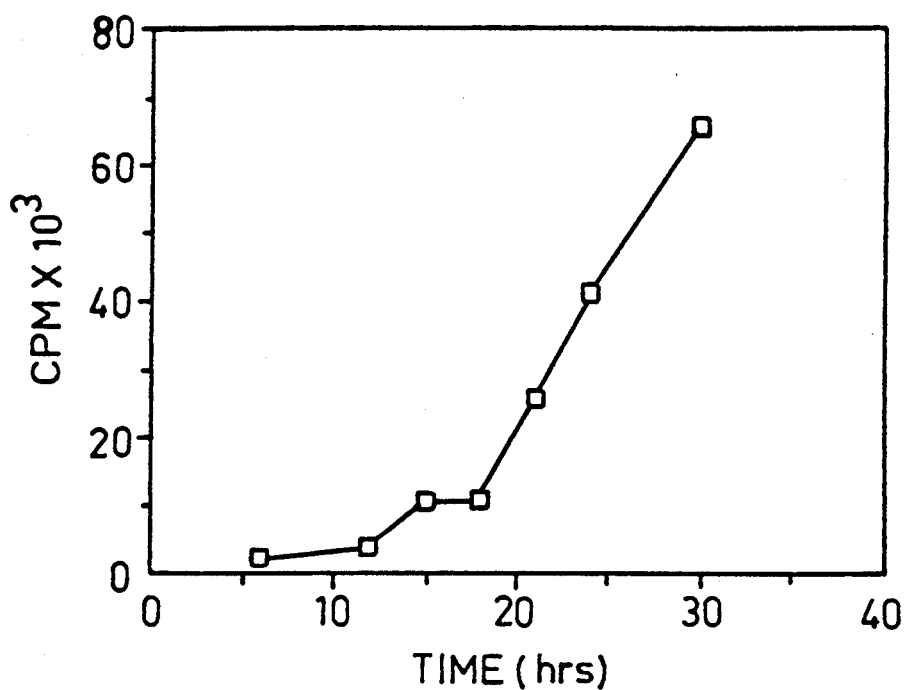
FIG. 3 is a graph showing the duration of the $G_1$-phase of the smooth muscle cell cycle.

The effect of gamma-interferon on smooth muscle cell replication was further elucidated by analysis of $^3$H-thymidine uptake by synchronized cells during and after entry into the cell cycle (see FIG. 3). First, the duration of the $G_1$ phase of the cell cycle was determined. Cells in 10-cm$^2$ Petri dishes were growth-arrested by serum starvation, and then induced to enter the cell cycle at 0 hours by addition of 10% fetal calf serum. $^3$H-thymidine was added together with fetal calf serum, cells were harvested at various points of time, and trichloroacetic acid-insoluble radioactivity determined by scintillation counting of triplicate cultures. The time from serum addition to the start of $^3$H-thymidine uptake was determined (i.e. the inflection point of the curve in FIG. 3). The $G_1$ phase was approximately 20 hours.

Figure 4:
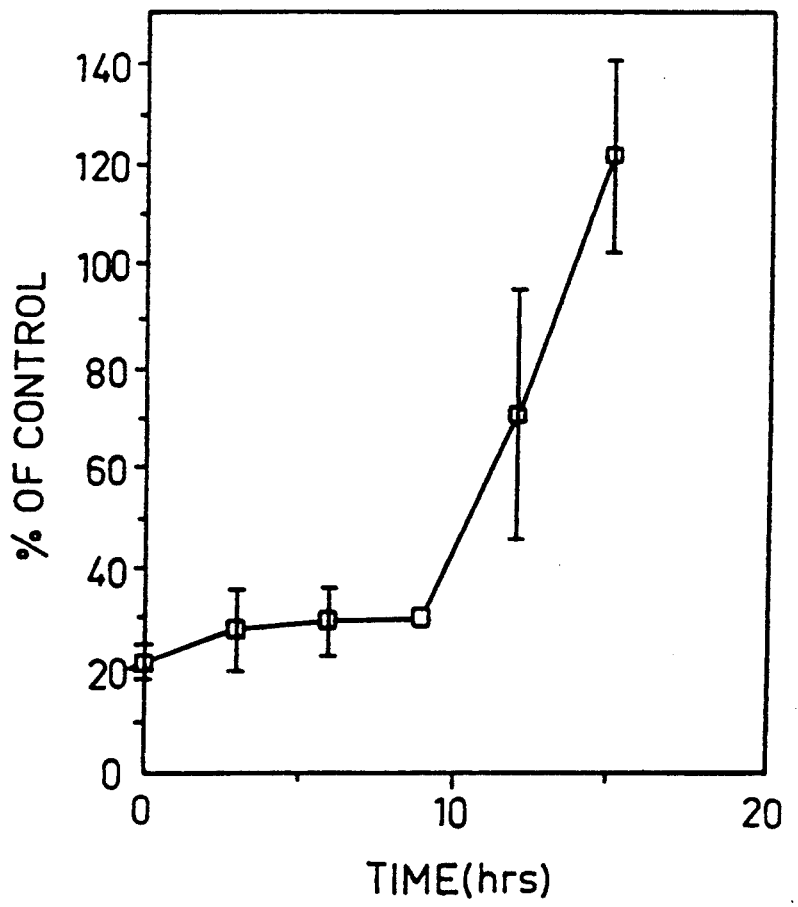
FIG. 4 is a graph showing the effect of gamma-interferon on smooth muscle cell replication in an early phase of the cell cycle.

With reference to FIG. 4 it is shown that when gamma-interferon is added together with serum, the uptake of $^3$H-thymidine is reduced by 70%. Gamma-interferon inhibits smooth muscle cell replication by acting at an event in early $G^1$ of the cell cycle. Cells in 10-cm$^2$ Petri dishes were growth-arrested, and then induced to enter the cell cycle by addition of FCS. They were continuously exposed to 3H-thymidine from then on. Gamma-interferon was added together with FCS, or 3, 6, 9, 12 or 15 hours later. All cells were harvested at 24 hours, and tricloroacetic acid-insoluble radioactivity determined by scintillation counting of quadruplicate cultures. The x-axis shows the time from addition of FCS to addition of gamma-interferon, with "0 hrs" representing the cultures that received FCS and gamma-interferon simultaneously, and "15 hrs" the cultures that received gamma-interferon 15 hours after the addition of fetal calf serum. On the y-axis, 100% represents the $^3$H-radioactivity in cultures that were never exposed to gamma-interferon, and the radioactivity in gamma-interferon treated cultures is given in percent of this value (mean ±SD). If, however, the addition of gamma-interferon was delayed more than 9 hours after the addition of serum, no inhibition was seen (see FIG. 4). The data therefore suggest that gamma-interferon acts by blocking the transition from $G_0$ to $G_1$ or an early event during the $G_1$ phase of the cell cycle in vascular smooth muscle cells.

Gamma-interferon induces expression of Ia antigens by a variety of target cells, including endothelial cells and fibroblasts. Smooth muscle cells at atherosclerotic arteries were observed to express these antigens (see Jonasson L., Holm J., Skalli O., Gabbiani G., Hansson G. K.: Expression of class II transplantation antigen on vascular smooth muscle cells in human atherosclerosis. J Clin Invest 1985:76:125–131), and the presence of activated T lymphocytes in atherosclerotic plaques suggested that gamma-interferon released from the T lymphocytes may induce expression of this antigen (see Jonasson L., Holm J., Skalli O., Gabbiani G., Hansson G. K.: Expression of class II transplantation antigen on vascular smooth muscle cells in human atherosclerosis. J Clin Invest 1985:76:125–131 and Hansson G. K., Jonasson L., Holm J., Claesson-Welsh L.: Class II MHC antigen expression in the atherosclerotic plaque; smooth muscle cells express HLA-DR, HLA-DQ, and the invariant gamma chain. Clin Exp Immunol 1986:64:261–268). This possibility was now tested by exposing cultured smooth muscle cells to gamma-interferon.

Figure 5:
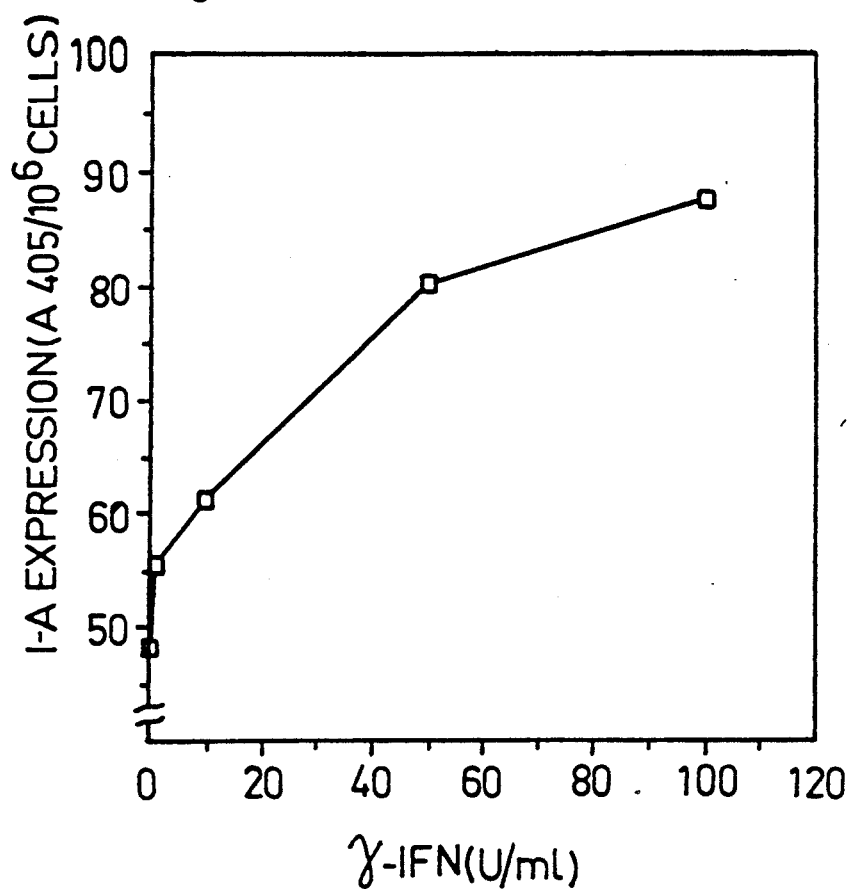
FIG. 5 is a graph showing the effect of gamma-interferon on I-A expression in smooth muscle cells at different gamma-interferon concentrations.

FIG. 5 shows that gamma-interferon (gamma-IFN) induces cell surface I-A expression on smooth muscle cells in a dose-dependent fashion. Cells in 96-well microtiter plates were treated with recombinant murine gamma-interferon at various concentrations for three days, and then assayed for I-A expression by the enzymelinked immunoassay technique. I-A expression per cell was calculated by dividing the total I-A value in each culture (absorbance units at 405 nm) with the number of cells per culture as determined by dye binding. Means of cultures (n=16) are shown; the variation coefficients were always less than 2%.

Figure 6:
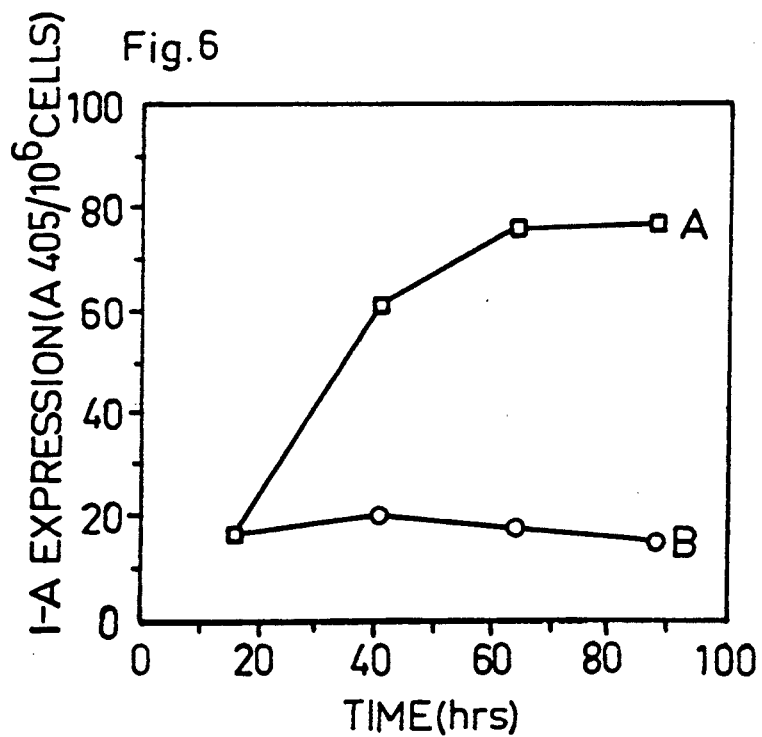
FIG. 6 is a graph showing the time dependent effect of gamma-interferon on I-A expression in smooth muscle cells.

In FIG. 6 the time course of gamma-interferon-induced smooth muscle I-A expression is demonstrated. Cells in 96-well microtiter plates (n=16) were treated with gamma-interferon (gamma-IFN stim; 100 units/ml), and cell surface I-A expression was analyzed by enzymelinked immunoassay at various points of time after addition of gamma-interferon (A). I-A expression per cell was determined by dividing I-A expression per well ($A_{405}$ units) with the cell number per well. Control values (B) are derived from unsimulated cells. Standard deviations were below 2% of means. Induction was detectable after 40 hours of exposure to gamma-interferon and a plateau was reached after 60 hours of stimulation. The time frame of induction of I-A expression clearly parallelled the growth inhibition induced by gamma-interferon.

Figure 7:
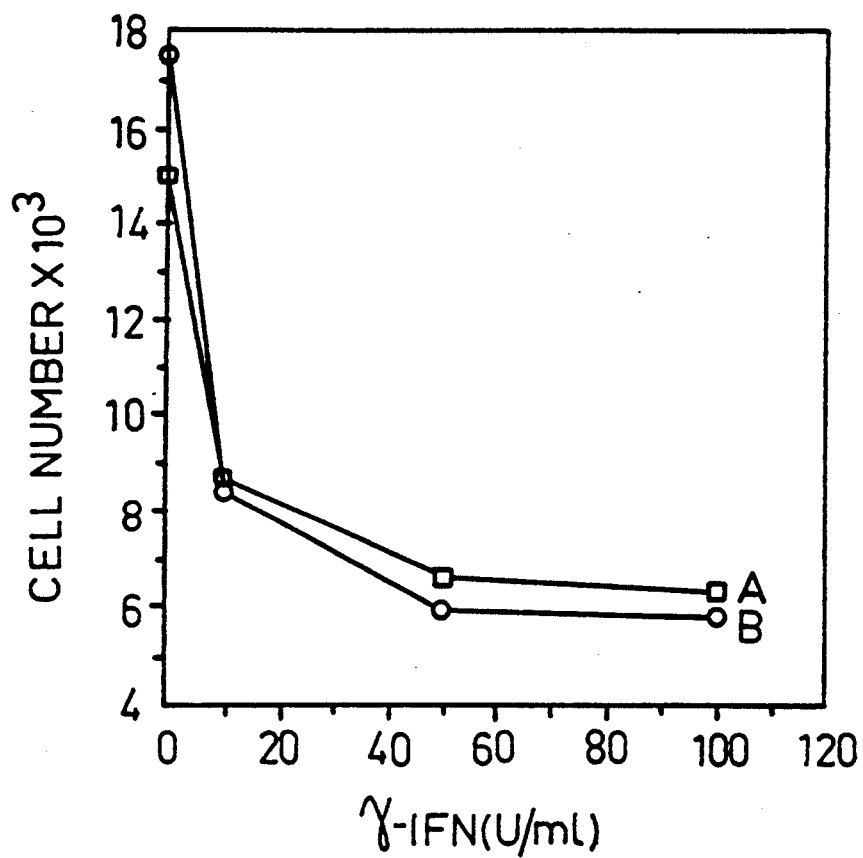
FIG. 7 is a graph showing the lack of endotoxin contamination in gamma-interferon preparations used for inhibition of smooth muscle cell proliferation.

With reference to FIG. 7 it is shown that the effects of gamma-interferon on growth and I-A expression are not due to contaminating endotoxins since endotoxin inhibition by polymyxin B added together with gamma-interferon did not affect the results. Growth-synchronized cells were incubated with recombinant gamma-interferon at various concentrations, with (B) or without (A) the addition of polymyxin B (50 μg/ml). Means of 16 parallel cultures in 96-well microtiter plates are shown; the coefficient of variation was below 2%. Pm refers to polymyxin B. The effects on growth and Ia expression obtained with mouse gamma-interferon (produced by Genentech) were identical to those obtained with recombinant rat gamma-interferon (produced by Holland Biotechnology). In contrast, human gamma-interferon did not induce Ia expression in rat cells.

The in vitro observations of simultaneous gamma-interferon induced inhibition of cell proliferation and expression of I-A antigen prompted the testing of the hypothesis that growth inhibition and I-A expression are related phenomena also in vivo. Therefore, smooth muscle proliferation in the rat carotid artery was induced by balloon catheter injury, and all replicating cells from the time of injury and onwards were labeled with $^3$H-thymidine delivered continuously via an osmotic pump. Cell replication and I-A expression were analyzed 14 days after injury when the intimal thickening is established but proliferation still continues. The results are given in Table I below.

TABLE I

| Cell Replication and Ia Expression in Proliferative Intimal Lesions During the 14-Day $^3$H-thymidine Labeling Period | | |
|---|---|---|
| | $^3$H-thymidine+ | $^3$H-thymidine− |
| I-A+ | 1.3 (1.4) | 9.6 (6.2) |
| I-A− | 80.6 (4.1) | 8.5 (8.9) |

Values in percent of total number of cells, mean ±SD in parentheses.

Of the intimal smooth muscle cells, 81.9% were $^3$H-thymidine positive, indicating that they had gone through at least one cycle of cell replication. I-A, detectable by immunocytochemistry, was expressed in 10.9% of the cells. While the majority of all intimal smooth muscle cells were labeled with $^3$H-thymidine, only one eighth of the I-A positive cells were $^3$H-thymidine positive. Among $^3$H-thymidine-negative smooth muscle cells, more than half were I-A positive.

The correlation between DNA replication and I-A expression was also analyzed during the fourteenth day following surgery, by injecting $^3$H-thymidine as a 24-hour pulse immediately before the animals were killed. In this case, 25.5% of the cells were $^3$H-thymidine positive, but none of these cells expressed I-A. These results are given in Table II.

TABLE II

| Cell replication and Ia Expression in Proliferative Intimal Lesions During the 24-Hour $^3$H-thymidine Labeling Period | | |
|---|---|---|
| | $^3$H-thymidine+ | $^3$H-thymidine− |
| I-A+ | 0 (0) | 5.8 (2.2) |
| I-A− | 25.5 (4.2) | 68.7 (6.4) |

Values in percent of total number of cells, mean ±SD in parentheses.

Figure 8:
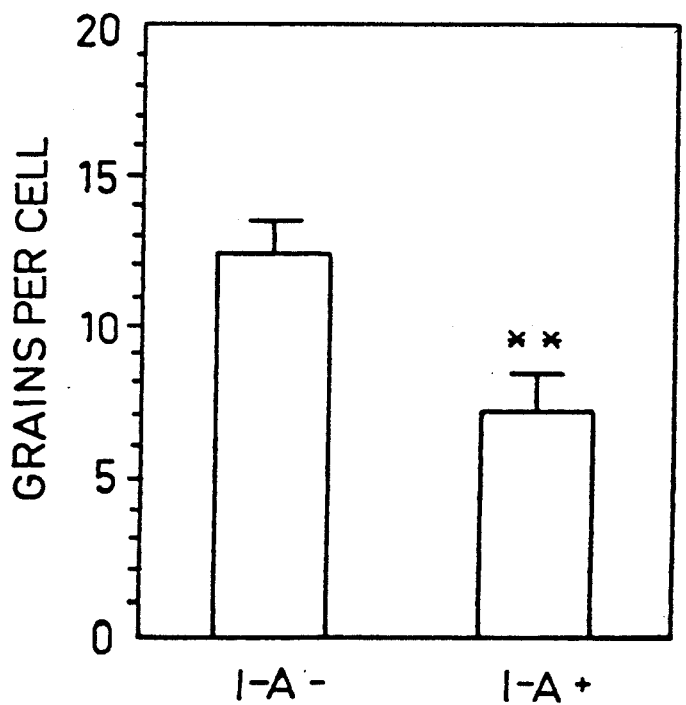
FIG. 8 is a diagram showing the extent of replication of I-A expressing smooth muscle cells and I-A negative ones, respectively.

The inverse correlation between DNA replication and I-A expression suggested that the mechanism that induces I-A expression also inhibits proliferation. This idea was supported by a detailed analysis of the autoradiograms obtained from rats labeled by the 14-day osmotic pump regimen. With reference to FIG. 8 it is shown that I-A expressing smooth muscle cells undergo fewer replications than I-A negative ones in the neointima during the response to injury. Arterial injury was inflicted by carotid ballooning of rats, and replicating cells were labeled by $^3$H-thymidine continuously infused via osmotic pumps over 14 days. I-A expression was determined by immunocytochemistry and $^3$H-thymidine uptake by autoradiography of the same section. The number of silver grains over I-A positive and I-A negative cells was counted in four lesions (50 I-A positive and 50 I-A negative cells per lesion). Since there was no significant difference between animals, the data from all five lesions were pooled for the statistical analysis The difference in silver grains between I-A positive and I-A negative cells is different at p<0.01, and mean ±SD are indicated in the figure. In the $^3$H-thymidine-labeled, proliferating population of cells, the average number of silver grains per nucleus was almost twice as high in I-A negative cells when compared with I-A positive cells. More $^3$H-thymidine would be expected to accumulate in cells with each additional proliferation cycle and the grain number per cell is closely related to the radioactivity per cell. The difference between I-A positive and I-A negative smooth muscle cells therefore implies that I-A positive cells underwent fewer cycles of DNA synthesis than did smooth muscle cells that did not express I-A (for discussion of this type of analysis, see Clowes A. W., Schwartz S. M.: Significance of quiescent smooth muscle migration in the injured rat carotid artery. Circ Res 1985:56:139–145).

Animal Experiment II

A pilot in vivo experiment was carried out, which included eight 400-g male Sprague-Dawley rats. An intimal lesion was inflicted in the common carotid artery with a Fogarty 2F balloon catheter as previously described. Four of the rats received recombinant rat gamma-interferon at 200,000 U s.c. daily for seven days, and the other four rats were injected with the same volume of vehicle (sodium chloride solution).

All rats were sacrificed fourteen days after ballooning, and fixed by perfusion with 1% paraformaldehyde in phosphate buffer. The operated (left) and unoperated (right) carotids were embedded in OCT medium and snap-frozen in n-hexane/liquid nitrogen. 10 μm cryostat sections were cut at every 100 μm, and the area occupied by the neointima was determined by morphometry using the point-sampling method. The results are summarized in Table III.

TABLE III

| Neo-intima in gamma-interferon treated and control rats | | | |
|---|---|---|---|
| Treatment | n | a | s.d. | P |
| gamma-IFN | 4 | 2.30 | 1.00 | <0.01 |
| Control | 4 | 4.80 | 0.50 | | n is the number of rats and a is the cross-sectional area in square micrometers. Statistical analysis by Student's t test.

It is clear that treatment with gamma-interferon significantly inhibited the development of the intimal thickening, and it is noteworthy that this inhibition persisted one week after cessation of treatment with gamma-interferon. This supports the hypothesis that medial cells are committed to replication and migration at a critical point of time after injury. Inhibition of proliferation at this point of time appears to persistently reduce the size of the lesion.

The above experiments clearly show the inhibiting effect of gamma-interferon on smooth muscle cell replication.

Gamma-interferon may thus be used for the treatment of vascular stenosis caused by e.g. intimal hyperplasia and in a preferred embodiment for the treatment of arterial stenosis following vascular surgery and/or angioplasty. Gamma-interferon should be administered to a patient in a pharmaceutical preparation containing said interferon in a sufficient amount to produce a therapeutical effect. The actual dose and treatment period required in a specific case will be decided by the attending physician. The dose should be sufficient to induce the expression of class II-MHC antigens on target cells, e.g. keratinocytes.

Gamma-interferon is defined herein as a polypeptide having the sequence of native gamma-interferon as set forth in European Publication No. 77 670 and all amino acid sequence or other variants thereof which are capable of inhibiting stenosis by the methods described herein or their analogues using cells from other animals. Examples of such variants are alleles or the products of site directed mutagenesis in which amino acid residues are deleted, inserted or substituted. For example, see European Publication No. 146 354. For veterinary therapy, gamma-interferon should be used which is homologous to or active in the animal species to be treated. In human therapy, the desCysTyrCys variant of the sequence shown in EP 77 670 should be employed, and optionally the C-terminal variant in which the last 4 resides are deleted in post-translational processing. Gamma-interferon having native sequences can be obtained by purification from natural sources using known methods. The same molecule or its variants can be obtained from recombinant sources, also by known methods.

A typical formulation contains gamma-interferon (20×10f6) at 1.0 or 0.2 mg/ml, succinic acid 0.27 mg/ml, disodium succinat hexahydrate 0.73 mg/ml, mannitol 40 mg/ml, polysorbate 20 0.1 mg/ml qs to 1 g water for injection/ml at pH 5.0. This aqueous formulation is administered at therapeutic doses, which will be less than the maximum tolerated doses in humans as determined by the clinician. Gamma-interferon also can be administered from a reconstituted lyophilized preparation.

Gamma-interferon is administered by any conventional route that will direct a therapeutic dose to the site of intimal injury, for example, by intravenous or intrapulmonary (EP 257 956) delivery routes. Administration may be by continous infusion or bolus dosing sufficient to maintain therapeutic levels. The gamma-interferon should be used at least in the course of the events leading to stenosis if possible and continued thereafter for a time sufficient to permit proper healing of the vasculature, typically about from 3 to 10 days as determined by the clinician.

We claim:

1. A method of using gamma-interferon for the treatment of vascular stenosis, wherein gamma-interferon is administered to a patient having vascular stenosis in a pharmaceutical preparation containing said interferon in a sufficient amount to inhibit growth or proliferation activity of arterial smooth muscle cells.

2. The method of using gamma-interferon according to claim 1, wherein the treatment of vascular stenosis is the treatment of restenosis following the treatment of arterial stenosis or occlusion.

3. The method of using gamma-interferon according to claim 2, wherein the treatment of restenosis is the treatment of arterial stenosis following vascular surgery and/or angioplasty.

4. The method of claim 1 wherein the gamma-interferon is desCysTyrCys gamma-interferon.

5. The method of claim 4 wherein the last four (4) C-terminal residues of the full length sequence of the desCysTyrCys gamma-interferon are deleted.

* * * * *